United States Patent [19]
Friedman et al.

[11] Patent Number: 5,744,155
[45] Date of Patent: Apr. 28, 1998

[54] BIOADHESIVE EMULSION PREPARATIONS FOR ENHANCED DRUG DELIVERY

[76] Inventors: Doron Friedman, 33 Alon, Carmei Yosef; Joseph Schwartz, 40 Benjamin Street; Shimon Amselem, 38 Benjamin, both of Rehovot, all of Israel

[21] Appl. No.: 106,262

[22] Filed: Aug. 13, 1993

[51] Int. Cl.$^6$ .................................................. A61K 9/107
[52] U.S. Cl. .................... 424/434; 424/435; 424/436; 424/450; 514/937; 514/938
[58] Field of Search .................. 424/434, 435, 424/436, 450, 484; 514/937, 938

[56] References Cited

U.S. PATENT DOCUMENTS

| | | |
|---|---|---|
| 4,548,922 | 10/1985 | Carey et al. .................. 514/4 |
| 5,055,303 | 10/1991 | Riley, Jr. .................. 424/436 |
| 5,120,710 | 6/1992 | Liedtke .................. 514/3 |
| 5,188,837 | 2/1993 | Domb .................. 424/450 |

FOREIGN PATENT DOCUMENTS

| | | |
|---|---|---|
| 0 115 627 | 12/1983 | European Pat. Off. . |
| 0 140 085 | 9/1984 | European Pat. Off. . |
| 0 442 671 | 2/1991 | European Pat. Off. . |
| 0 494 654 | 1/1992 | European Pat. Off. . |
| 2 127 689 | 8/1983 | United Kingdom . |
| 90/03164 | 4/1990 | WIPO . |
| 91/05545 | 5/1991 | WIPO . |
| 91/14454 | 10/1991 | WIPO . |
| 92/03121 | 3/1992 | WIPO . |
| 92/18147 | 10/1992 | WIPO . |
| 93/00076 | 1/1993 | WIPO . |
| 93/00077 | 1/1993 | WIPO . |
| 94/03157 | 7/1993 | WIPO . |

OTHER PUBLICATIONS

Longer, M.A. and J.R. Robinson. (1986). *Pharmacy International*, May Issue, pp. 114–117.
Nagai, T. and Y. Machida. (1985). *Pharmacy International*, Aug. Issue, pp. 196–200.
*J. Pharm. Parmacol* (1992), 44 (Suppl. 1): 186–190.
*Meth Find Exp Clin Parmacol* (1991), 13(3): 205–220.

*Primary Examiner*—Raj Bawa

[57] ABSTRACT

The invention relates to an oil-in-water emulsion and related method for administration of a drug to a mucosal surface. The emulsion has an aqueous continuous phase and a plurality of submicron particles having an average particle diameter of from 10 nm to 600 nm, with the particles having a hydrophobic core of a fat or oil which is surrounded by a surfactant layer. The emulsion further includes a drug and a mucoadhesive polymer which is a polymer or copolymer of acrylic acid or methacrylic acid, a poly(methyl vinyl ether/maleic anhydride) copolymer, pectin, alginic acid, hyaluronic acid, chitosan, gum tragacanth, karaya gum or carboxymethylcellulose. The hydrophobic core has less than 1% (w/w) protein, relative to the weight of the hydrophobic core, and the emulsion contains less than 5% (w/w) surfactant, relative to the weight of the hydrophobic core.

42 Claims, 7 Drawing Sheets

BIOADHESIVE EMULSION PREPARATIONS FOR ENHANCED DRUG DELIVERY

1. FIELD OF THE INVENTION

The present invention relates to bioadhesive emulsions useful as pharmaceutical compositions for enhanced drug delivery into or through bodily mucous membranes, such as corneal, conjunctival, buccal, sublingual, nasal, pulmonary, stomachic, intestinal, rectal, uterine, bladder and vaginal mucosa.

2. BACKGROUND OF THE INVENTION

Bioadhesion is the characteristic of certain natural and synthetic polymers of binding to various biological tissues. Of particular interest are polymers which bind to the mucous lining that covers the surface of many tissues which communicate directly or indirectly with the external environment, such as the gut, respiratory tract, reproductive organs, and cornea. Mucus binding polymers may be referred to as mucoadhesive.

Several bioadhesive, and specifically mucoadhesive, polymers are known. The chemical properties of the main mucoadhesive polymers are summarized as follows:

a. strong H-bonding groups (—OH, —COOH) in relatively high concentration;

b. strong anionic charges;

c. sufficient flexibility of polymer backbone to penetrate the mucus network or tissue crevices;

d. surface tension characteristics suitable for wetting mucus and mucosal tissue surfaces; and e. high molecular weight.

Bioadhesive polymers currently used in pharmaceutical preparations include: carboxymethylcellulose (CMC), hydroxypropylmethylcellulose (HPMC), polyacrylic and polymethacrylic acid and their derivatives, pectin, alginic acid, chitosan, polyvinylpyrrolidone, hyaluronic acid, and polyvinyl alcohol. The most frequently used polymer is Carbopol (Carbomer), which is a high molecular weight polyacrylic acid polymer. It is used in many formulations for bioadhesive drug delivery systems, as a suspending agent, as a tablet coating, and in ocular suspensions.

Carbopol forms thixotropic mixtures with water at pH above 6.5 and at concentrations as low as 0.25–0.3% in water. The gel-forming properties of Carbopol strongly depend on salt concentration and ionic strength of the formulation. The drug delivery enhancing effect of Carbopol on coated tablets may be due to both the polymer-mucus interaction and the prolongation of residence time due to increased viscosity.

Many workers have investigated the effect of pH on the interaction of polyacrylic acid with mucus, noting that the adhesion of acrylic-based polymers to mucous membrane is greater at pH <6. Protonation of the carboxyl groups (pKa 4.75) permits H-bonding between the polymer and the mucin network, resulting in enhanced retention of the polymer in contact with a mucosal surface.

Several reports of liposome suspensions containing bioadhesive polymers have been published recently. Interaction between mucoadhesive polymers and phospholipid vesicles has, in turn, resulted in the prolonged corneal residence of those vesicles.

The biological effects of incorporating bioadhesive polymers into drug formulations can be tested by various methods, such as increased retention time while in the eye or increased effective drug concentration. One of the models for bioadhesion testing involves interaction of the drug delivery system under investigation with ocular surfaces such as conjunctiva or cornea. A new ocular formulation of the beta-blocker betaxolol, "Betoptic S," contains the drug absorbed on micropowdered cation exchange resin suspended in aqueous solution with Carbopol. Carbopol in this formulation is a suspending and viscosity regulating agent.

Corneal retention of Carbopol coated phosphatidylcholine liposomes is significantly greater compared with uncoated liposomes, especially at pH 5.0. In a model study, the miotic agent tropicamide was employed in a liposomal formulation; Davies et al., *J. Pharm. Res.* (1992) 9:1137–1144. The pH-dependent lecithin-polyacrylic binding, followed by complex formation, was described for three liposome preparations. It was found that every phosphatidylcholine vesicle was coated with a swollen gel layer, and the mean particle size increased from 260 to 1300 nm. Such modification decreased the rate of drug release from liposomes and increased retention time of liposomes in the eye, but no significant differences were found in activity and bioavailability between the drug in solution and in Carbopol-coated liposomes.

In EPA 0028110, polyacrylic acid derivatives are claimed as stabilizers for pharmaceutical emulsions. Carbopol in such compositions, at concentrations near the gel-point and at neutral pH, stabilizes the emulsion. Final preparations exhibited a viscosity of 66–132 centipoise, and could be autoclaved. Bioadhesive properties were not reported and would not be expected, since in all examples the emulsions were adjusted to pH 7, at which mucosal binding is minimal.

Zerbe et al., WO 93/00076, disclose a drug delivery system of microparticles having a spherical core composed of a biopolymer, preferably a protein such as albumin or gelatin, which typically has been crosslinked or denatured to maintain its structural coherency. The spherical core is suggested to be combined with a bioadhesive polymer.

Riley, U.S. Pat. No. 5,055,303, discloses a bioadherent emulsion of the water-in-hydrophobic phase type wherein the continuous hydrophobic phase is a solid fat. Bioadhesion is not attributed to a specific adherent component, but rather is apparently ascribable to the viscosity of the solid continuous phase.

3. SUMMARY OF THE INVENTION

The present invention provides novel compositions and methods for enhancing bioadhesive properties of lipid-in-water type emulsions containing drugs or other biologically active compounds.

The emulsion comprises a colloidal dispersion of droplets or particles having a hydrophobic core and containing a bioadhesive, preferably mucoadhesive, macromolecule. In preferred embodiments, the emulsion contains a biologically active agent, which may be distributed between the hydrophobic and aqueous phases of an oil-in-water type emulsion, or may be present predominately in one of the phases. In certain embodiments the emulsion is stabilized with amphiphilic and/or non-ionic surfactants.

The present emulsions are adapted for application to a mucosal surface of a vertebrate animal, preferably a mammal, including humans. These compositions improve the permeability and bioavailability of active compounds after application to a mucous surface. Mucosal surfaces of interest include the corneal, conjunctival, nasal, buccal, sublingual, pulmonary, stomachic, intestinal, uteral, bladder, rectal and vaginal mucosa.

4. BRIEF DESCRIPTION OF THE FIGURES

5. DETAILED DESCRIPTION OF THE INVENTION

Figure 1A:
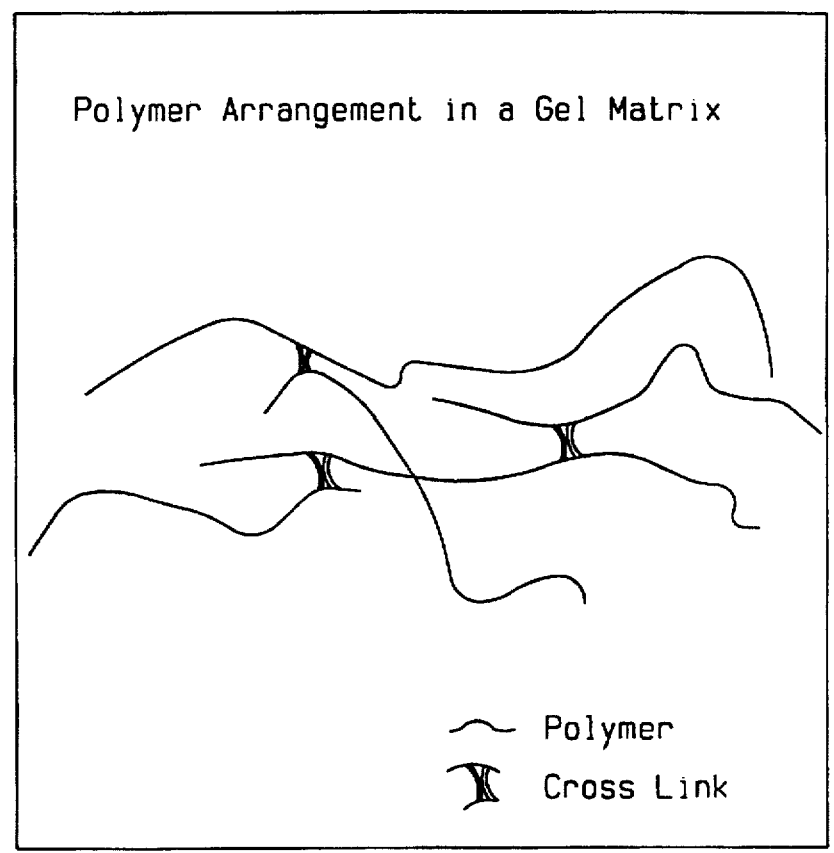
FIG. 1 illustrates some of the differences among a cross-linked polymer gel matrix (A), a conventional oil-in-water emulsion (B), an emulsion of oil droplets diffusing in a gel matrix (C), and bioadhesive coated emulsion particles of an aspect of the present invention (D).
Figure 1B:
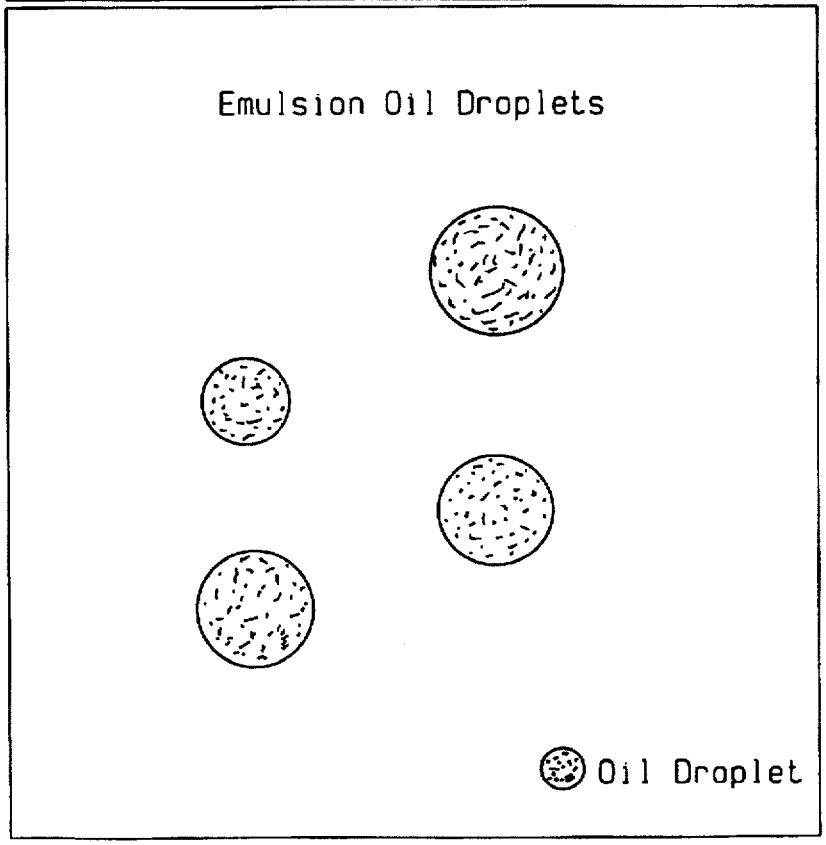
Figure 1C:
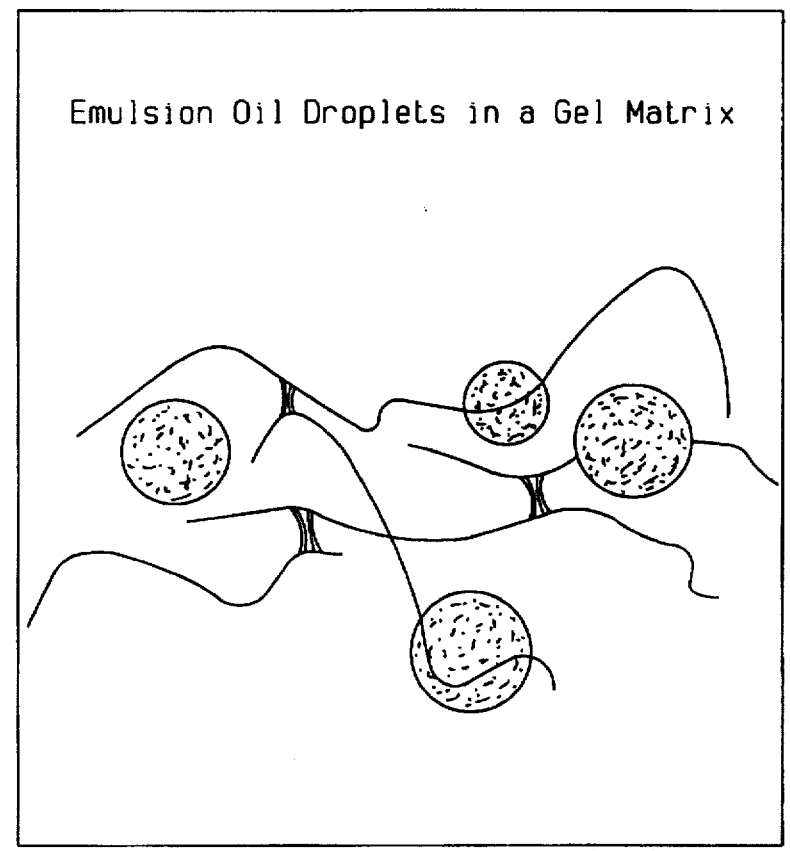
Figure 1D:
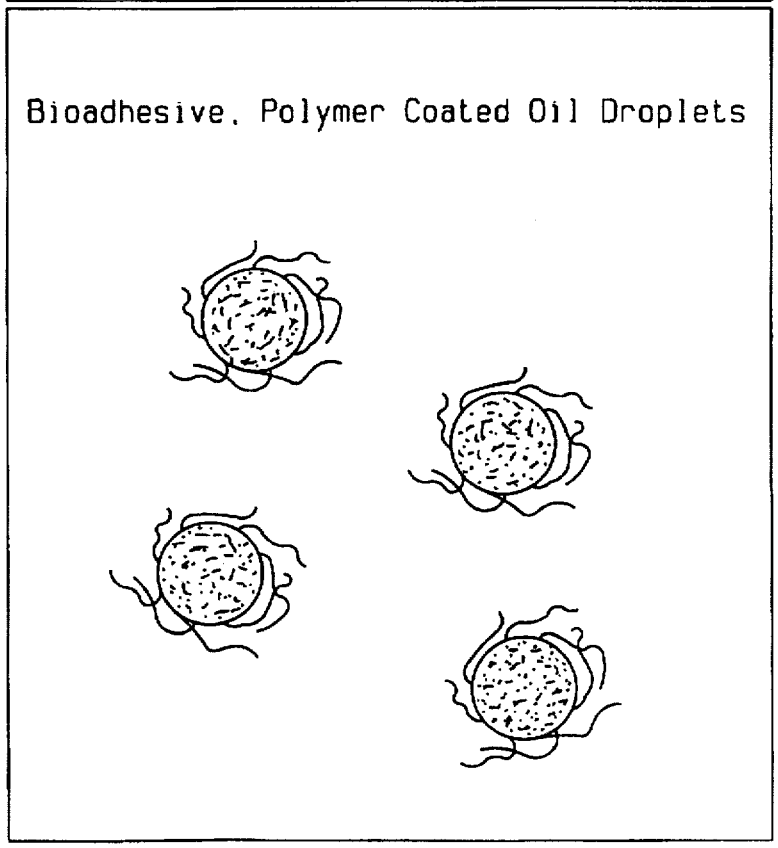

Use of bioadhesive polymers in pharmaceutical emulsions affords enhanced delivery of drugs in bioadhesive polymer-coated suspensions. Bioadhesive pharmaceutical emulsions: a) prolong the residence time in situ, thereby decreasing the number of drug administrations required per day; and b) may be localized in the specified region to improve and enhance targeting and bioavailability of delivered drugs.

The ability to retain and localize a drug delivery emulsion in a selected region leads to improved bioavailability, especially for drugs exhibiting a narrow window of adsorption due to rapid metabolic turnover or quick excretion. Intimate contact with the target absorption membrane improves both the extent and rate of drug absorption.

5.1. Features of the Emulsion Particles

The bioadhesive emulsions of the present invention comprise an aqueous continuous phase suspending a colloidal phase of submicron particles. The particles have a weighted average diameter of 10 to 600 nm, more preferably 30 to 500 nm, most preferably 70 to 300 nm. In many embodiments, the weighted average diameter will be less than 450 nm, 400 nm, 300 nm, or 200 nm. Usually the diameter will be greater than 40 nm or 50 nm, and frequently is greater than 70 nm. Often the above-stated upper and lower diameter ranges will include both the weighted average and at least one standard deviation of particle diameter.

The emulsion particle comprises a hydrophobic core, often including or even consisting essentially of triglyceride. Optionally other hydrophobic lipids may be used, including cholesterol or cholesteryl esters, paraffin, mineral oil, silicone oil, and waxes. Usually the core of the particles will be substantially free of protein, i.e., less than 1% (w/w), and in most cases less than 0.1% protein.

The emulsion usually further comprises at least one surfactant, which may be a natural biologically compatible surfactant such as phospholipid (e.g., lecithin) or a pharmaceutically acceptable nonnatural surfactant such as Tween-80. The surfactant assists in maintaining particles within the desired size range and preventing their aggregation.

In many embodiments the emulsion may be formed and stabilized in the substantial absence of one or more cosurfactants selected from the group consisting of an unhalogenated aliphatic C3–C6 alcohol, a free fatty acid, a mono- or di-glyceride, a polyglycerol fatty acid ester (e.g., Plurol), or a lysophosphatidyl choline. One or all of the above-named cosurfactants may comprise less than 5%, commonly less than 1%, and frequently less than 0.1% (w/w) relative to the weight of the hydrophobic core.

The emulsion further comprises a bioadhesive, usually mucoadhesive, polymer. The polymer frequently may contain multiple carboxylic acid moieties, e.g., polyacrylates, alginic acid, hyaluronic acid, pectin, or carboxymethylcellulose. Polymers bearing polyamine groups also are capable of binding to mucin, e.g., chitosan. Certain mucin-binding polymers are uncharged, e.g., hydroxypropylmethyl cellulose.

In many cases, the bioadhesive polymer is believed to coat or form a layer on the outer surface of the particle core, possibly in association with the surfactant. Frequently the addition of the bioadhesive polymer increases the mean particle diameter of the emulsion, as may be seen, e.g., in Examples 3, 8–9, and 13. This result is consistent with the "coating" model of polymer-core interaction, since the added polymer layer would be expected to result in a greater diameter. However, in other cases the added polymer makes little difference in, or actually decreases, particle diameter; see, e.g., Examples 4–5, 6–7, 17, and 21. In these circumstances, the polymer may have surfactant as well as mucous-binding properties, thereby inserting itself deeply into the surfactant interface. In extreme cases, the polymer may be sufficiently surface-active to reduce the average hydrophobic core diameter by increasing the effective surfactant-to-lipid ratio.

Regardless of the detailed molecular structure of the polymer-particle association, emulsions combining hydrophobic core and bioadhesive polymer are within the scope of the invention.

The continuous phase of the emulsion is aqueous, and may contain salts, sugars, antioxidants, preservatives, microbicides, buffers, osmoticants, cryoprotectants, and other pharmaceutically useful additives or solutes.

The emulsion also contains a biologically active compound, usually a drug, most commonly a prescription drug, although vitamins and other nonprescription medications also may be included. The active compound may be either hydrophilic or hydrophobic, since the emulsion provides a biphasic microenvironment.

5.2. Composition of the Hydrophobic Core

A hydrophobic compound which is suitably nontoxic for administration to mucosal surfaces may be used as a component of the core. Examples include triglycerides, preferably of food grade purity or better, which may be produced by synthesis or by isolation from natural sources. Natural sources may include animal fat or vegetable oil, e.g., soy oil, a source of long chain triglycerides (LCT). Other triglycerides of interest are composed predominantly of medium length fatty acids (C10–C18), denoted medium chain triglycerides (MCT). The fatty acid moieties of such triglycerides may be unsaturated, monounsaturated or polyunsaturated; mixtures of triglycerides having various fatty acid moieties are acceptable. The core may comprise a single hydrophobic compound or a mixture of compounds.

Other hydrophobic compounds which may be used include silicone oil, mineral oil, paraffin, and aliphatic and aromatic esters of hydrophobic acids, e.g., isopropyl myristate, benzyl benzoate, and tocopherol acetate. The ester category includes waxes, which often are composed of fatty acid moieties esterified with aliphatic alcohols, including C2–C6 short chain alcohols and C8–C22 fatty alcohols.

Optionally the core may contain cholesterol or cholesteryl esters. In many embodiments, cholesteryl esters or cholesterol comprise less than 10%, 5%, 1%, or even 0.1% (w/w) of the total hydrophobic components of the core.

Considerations in choice of core material include low toxicity and irritancy, biocompatibility, stability, and high loading capacity for biologically active compounds of interest such as drugs. Preferred hydrophobic core components have molecular weights below about 5,000 Da, more preferably below about 2,000 Da, and most preferably below about 1,500 Da. An exception is provided by silicone oils, which remain useful at much higher molecular weights.

5.3. Composition of Surfactant Component

Some embodiments of the invention provide an improved bioadhesive emulsion comprising incorporation of an amphiphilic and/or nonionic surfactant such as phosphatidylcholine, Tween, etc. The surfactant is believed in many embodiments to interact with the bioadhesive polymer to form a hydrated polymer film coating associated with the surfactant at the stabilized lipid/water interface surrounding the particle core.

Preferred compositions contain a surfactant component. The surfactant stabilizes the outer surface of the hydrophobic core component of the emulsion particles, thereby promoting a more uniform and manipulable particle size. Usually the surfactant is present in a proportion of 0.01% to 5% (w/w) of the emulsion, preferably 0.05% to 2%.

Typically, the weight percentage of surfactant relative to hydrophobic (oil or other lipid) component is from 0.2% to 50%, more preferably from 5% to 20%. Higher ratios of surfactant to core lipid tend to promote smaller particle core diameters.

Surfactants may be either natural compounds, such as phospholipids and cholates, or nonnatural compounds such as: polysorbates, which are fatty acid esters of polyethoxylated sorbitol (Tween); polyethylene glycol esters of fatty acids from sources such as castor oil (Emulfor); polyethoxylated fatty acid, e.g. stearic acid (Simulsol M-53); Nonidet; polyethoxylated isooctylphenol/formaldehyde polymer (Tyloxapol); poloxamers, e.g., poly(oxyethylene)poly (oxypropylene) block copolymers (Pluronic); polyoxyethylene fatty alcohol ethers (Brij); polyoxyethylene nonylphenyl ethers (Triton N); polyoxyethylene isooctylphenyl ethers (Triton X); and SDS. Mixtures of surfactant molecules, including mixtures of surfactants of different chemical types, are acceptable. Surfactants should be suitable for pharmaceutical administration and compatible with the drug to be delivered.

Particularly suitable surfactants include phospholipids, which are highly biocompatible. Especially preferred phospholipids are phosphatidylcholines (lecithins), such as soy or egg lecithin. Other suitable phospholipids include phosphatidylglycerol, phosphatidylinositol, phosphatidylserine, phosphatidic acid, cardiolipin, and phosphatidylethanolamine. The phospholipids may be isolated from natural sources or prepared by synthesis. Phospholipid surfactants are believed usually to form a single monolayer coating of the hydrophobic core.

In certain embodiments, the emulsion may be limited in or substantially free of one or more cosurfactants selected from the group consisting of free fatty acids, mono- or di-glycerides (fatty acid mono- or diesters of glycerol), aliphatic C3–C6 monoalcohols (exclusive of, e.g., chlorobutanol or other haloalkyl alcohol preservative), polyglycerol fatty acid esters (Plurol), or lysophosphatidyl choline. In many embodiments, the particular limited cosurfactant from the above group may constitute less than 5%, usually less than 1%, often less than 0.1%, relative to the weight of hydrophobic core component. In some embodiments, one or more cosurfactants may be present.

5.4. Bioactive Component

The pharmacological activity of a wide variety of drugs render them suitable for use in bioadhesive emulsion formulations, to treat a number of conditions. In general, those drugs suitable for topical application to external and internal ocular, vaginal, oral, buccal, nasal, pulmonary, and rectal mucous surfaces may be employed. Suitable drugs include, inter alia: antivirals (acyclovir, IUdR, ganciclovir, vidarabine, AZT), steroidal and non-steroidal anti-inflammatory drugs (dexamethasone, loteprednol, prednisolone derivatives, diclofenac, indomethacin, piroxicam etc.), antibiotics (e.g., ampicillin and erythromycin) antifungals (e.g., miconazole), vitamins, hormones, retinoic acid, local anesthetics, calcium channel blockers (e.g., Verapamil), prostaglandins and prostacyclins, antineoplastic and antimetabolitic drugs, miotics, cholinergics, adrenergic antagonists, anticonvulsants (e.g., phenytoin), antianxiety agents, major tranquilizers, antidepressants, anabolic steroids, estrogens, progesterones, and glycosaminoglycans (heparin, heparan, chondroitin sulfate, and low molecular weight derivatives thereof).

Descriptions of suitable drugs within these therapeutic classifications may be found in standard reference textbooks, such as Goodman and Gilman's *Pharmacological Basis of Therapeutics*, eighth edition (1990).

Many of the drugs listed above are poorly soluble in water and slowly adsorbed through mucous surfaces. Low bioavailability of such drugs severely limits their applicability, usage and effectiveness. Incorporation of such drugs into mucoadhesive emulsions of the present invention increases their bioavailability. Some exemplary drugs which would exhibit improved bioavailability when administered in a bioadhesive emulsion of the present invention include ampicillin, erythromycin, hydralazine, valproic acid, and verapamil.

5.4.1. Protein Components

In certain preferred preparations, the lipid particles of the inventive emulsions do not incorporate milk fat globule apolipoproteins or serum apolipoproteins such as apoB, apoAI, apoAII, or apoE. Lipid particles of the invention in certain preferred embodiments also are substantially free of intracellular marker proteins associated with the intracellular cytoskeleton (e.g., actin, myosin, troponin, tubulin, vimentin, and spectrin). Lipid particles which do not contain intracellular marker proteins are herein defined as "noncellular" particles, since they lack characteristic indicia of lipid particles present in or derived from cellular sources.

In most embodiments, the emulsion particles will be free or substantially free of the above or other proteins, i.e., less than 5%, usually less than 1%, and frequently less than 0.1% (w/w) protein relative to other particle components.

5.5. Bioadhesive Macromolecules

Emulsions of the present invention contain a bioadhesive macromolecule or polymer in an amount sufficient to confer bioadhesive properties. The bioadhesive macromolecule enhances the delivery of biologically active agents on or through the target surface. The bioadhesive macromolecule may be selected from acidic nonnaturally occurring polymers, preferably having at least one acidic group per four repeating or monomeric subunit moieties, such as poly(acrylic)- and/or poly(methacrylic) acid (e.g., Carbopol, Carbomer), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl)methylcellulose; basic amine-bearing polymers such as chitosan; acidic polymers obtainable from natural sources, such as alginic acid, hyaluronic acid, pectin, gum tragacanth, and karaya gum; and neutral nonnaturally occurring polymers, such as polyvinylalcohol; or their mixtures. The ionizable polymers may be present as free acids, bases, or salts, usually in a final concentration of 0.01–0.5% (w/vol).

Bioadhesive macromolecules often form viscous solutions, in addition to possessing more specific mucin binding properties. These effects may be distinguished by comparing the degree of adhesion to a mucin surface of a solution prepared with the putative bioadhesive macromolecule versus a similar control emulsion prepared with a non-bioadhesive macromolecule of comparable viscosity: for example, a starch or dextran solution. At similar viscosities, the emulsion prepared with a bioadhesive macromolecule will bind to the mucin surface more strongly than will the control emulsion prepared with the "nonbinding" macromolecule such as starch. Preferably, the bioadhesive macromolecule will produce at least 25% greater mucin binding than the control emulsion, more preferably at least 50% greater, still more preferably at least 100% greater mucin binding than the control emulsion. Either binding to mucin per se or amount or biological effect of the drug delivered may be used as a measurement parameter for bioadhesion. This test may be used to distinguish preferred bioadhesive molecules.

As used herein, a polymer of an indicated monomeric subunit contains at least 75%, preferably at least 90%, and up to 100% of the indicated type of monomer subunit; a copolymer of an indicated type of monomeric subunit contains at least 10%, preferably at least 25% of that monomeric subunit.

A preferred bioadhesive macromolecule is the family of acrylic acid polymers and copolymers, (e.g., CARBOPOL™). These contain the general structure:

One preferred group of polymers of acrylic acid is commercially available under the tradename Carbopol. Carbopol 934 is available in a pharmaceutical grade.

Preferred bioadhesive or mucoadhesive macromolecules have a molecular weight of at least 50 kDa, preferably at least 300 kDa, and most preferably at least 1,000 kDa. Favored polymeric ionizable macromolecules have not less than 2 mole percent acidic groups (e.g., COOH, $SO_3H$) or basic groups ($NH_2$, NRH, $NR_2$), relative to the number of monomeric units. More preferably, the acidic or basic groups constitute at least 5 mole percent, more preferably 10 mole percent, and still more preferably at least 25 or even 50, up to 100 mole % relative to the number of monomeric units of the macromolecule.

Preferred macromolecules also are soluble in water throughout their relevant concentration range (0.01–0.5% w/vol).

Incorporation of the bioadhesive macromolecule into the emulsion is believed to result in spontaneous association of the macromolecule with, and coating of, the emulsion particles, as in represented diagrammatically in FIG. 1. However, the resulting emulsion is within the scope of the invention regardless of the details of the microscopic particle structure.

5.6. Aqueous Solution

The aqueous solution constituting the continuous phase usually contains a biologically compatible buffer. Since bioadhesion of polymers having acidic groups is more pronounced at lower pH, the buffer is usually adjusted to the pH range 3–7, usually pH 3.5–6.5, more usually pH 4 to 6, frequently pH 4.5 to 5.5. Certain basic polymers having amine groups, such as chitosan, may be exposed to pH as low as 3 during preparation at the emulsion, although the usual pH range as administered is similar to or may be slightly higher than that for acidic polymers, i.e., pH 6–8.

Optionally, suitable chelating agents such as citric acid or EDTA may be present to minimize polyvalent or divalent cation binding to the acidic groups of the polymer. Other optional components may include, inter alia, antioxidants, antimicrobials, cryoprotectants, preservatives, salts, amino acids, and additives such as glycerol to adjust the solution tonicity.

In many embodiments, the aqueous solution is substantially free from sorbitol; i.e., the weight of sorbitol in the emulsion may be less than 10% (w/w) relative to the weight of hydrophobic core lipid, often less than 5%, commonly less than 1% or even 0.1%, and may be essentially absent. In many embodiments, the emulsion is also substantially free from phosphorylcholine, which, like sorbitol, may be limited to levels of 10%, 5%, 1%, or 0.1% (w/w) or less.

5.7. Dehydrated Emulsions

A further aspect of the invention provides dehydrated emulsions, made by dehydrating a bioadhesive emulsion of the type described herein. Dehydrated emulsions may be stored for prolonged periods with minimal degradation, then reconstituted with water shortly before use. Residual water content in the dehydrated emulsion is usually less than 5% (w/w), commonly less than 2%, and often less than 1%.

Dehydration may be performed by standard methods, such as drying under reduced pressure; when the emulsion is frozen prior to dehydration, this low pressure evaporation is known as lyophilization. Freezing may be performed conveniently in a dry ice-acetone or ethyl alcohol bath. The pressure reduction may be achieved conveniently with a mechanical vacuum pump, usually fitted with a liquid nitrogen cold trap to protect the pump from contamination. Pressures in the low millitorr range, e.g., 10–50 millitorr, are routinely achievable, but higher or lower pressures are sufficient.

A cryoprotectant or anticoalescent compound may be added to the emulsion prior to dehydration to inhibit flocculation and coalescence upon rehydration. The cryoprotectant may be of any type known in the art, including sugars and polysaccharides such as sucrose or trehalose, and non-natural polymers such as polyvinylpyrrolidone. Cryoprotectants are usually present at less than 25%, commonly 10%, more commonly 5%, 4% (w/v) or less in the emulsion before lyophilization.

A preferred category of cryoprotectants is amino acids and oligopeptides. Preferred amino acids include valine, leucine, isoleucine, lysine, methionine, threonine, serine, arginine, alanine, glycine, histidine, proline, phenylalanine, taurine, and carnitine, although any of the other natural amino acids may also be present. Amino acids may be of either D or L configuration, or a mixture; the natural L form is preferred. Amino acids may be present as their salts or esters, and as mixtures of amino acids or as pure species.

A particularly preferred amino acid is glycine, which may be present either in pure form or as a component of a mixture, e.g., in an hydrolyzate of collagen or other glycine-rich protein.

Mixtures of oligopeptides, especially di- and tripeptides, are another preferred type of cryoprotectant. These may be prepared conviently as partial protein hydrolyzates or enzymatic digests.

The amino acids or oligopeptides are generally present in the emulsion at a concentration of about 0.25 to 25% (w/w), preferably about 0.5 to 12% (w/w), more preferably about 1 to 10% (w/w), and commonly 3–6% (w/w).

Cryoprotectants and methods of making lyophilized emulsions are taught in more detail in copending application "Dry Compositions for Preparing Submicron Emulsions," attorney docket number 7754-010, assigned to Pharmos, which is herein incorporated by reference.

5.8. Methods of Preparation

A further embodiment of the invention relates to methods for preparation of a bioadhesive emulsion whereby the pH of the aqueous emulsion containing the bioadhesive polymer and the hydrophobic phase is adjusted to a level which promotes substantial, i.e. at least 90%, preferably at least 99%, or essentially complete ionization of the polymer. Thereafter the pH may be readjusted to a second level to enhance biocompatability or mucin binding, or to provide a stable storage environment prior to use. This process may be accomplished during or after incorporation of the bioadhesive polymer into the water phase, followed by emulsification together with the oil phase; alternatively, the bioadhesive polymer in water solution may be added to a prepared emulsion.

Usually the hydrophobic phase is homogenized in an aqueous phase by a pressure homogenizer, which facilitates production of smaller particle diameters which fall within the stated size range of the emulsions.

The pH is considered "adjusted" in this contemplation when the bioadhesive polymer and formed emulsion coexist or are combined at the relevant pH, regardless of the manner or sequence of steps by which the relevant pH was achieved in the combined emulsion.

Figure 2:
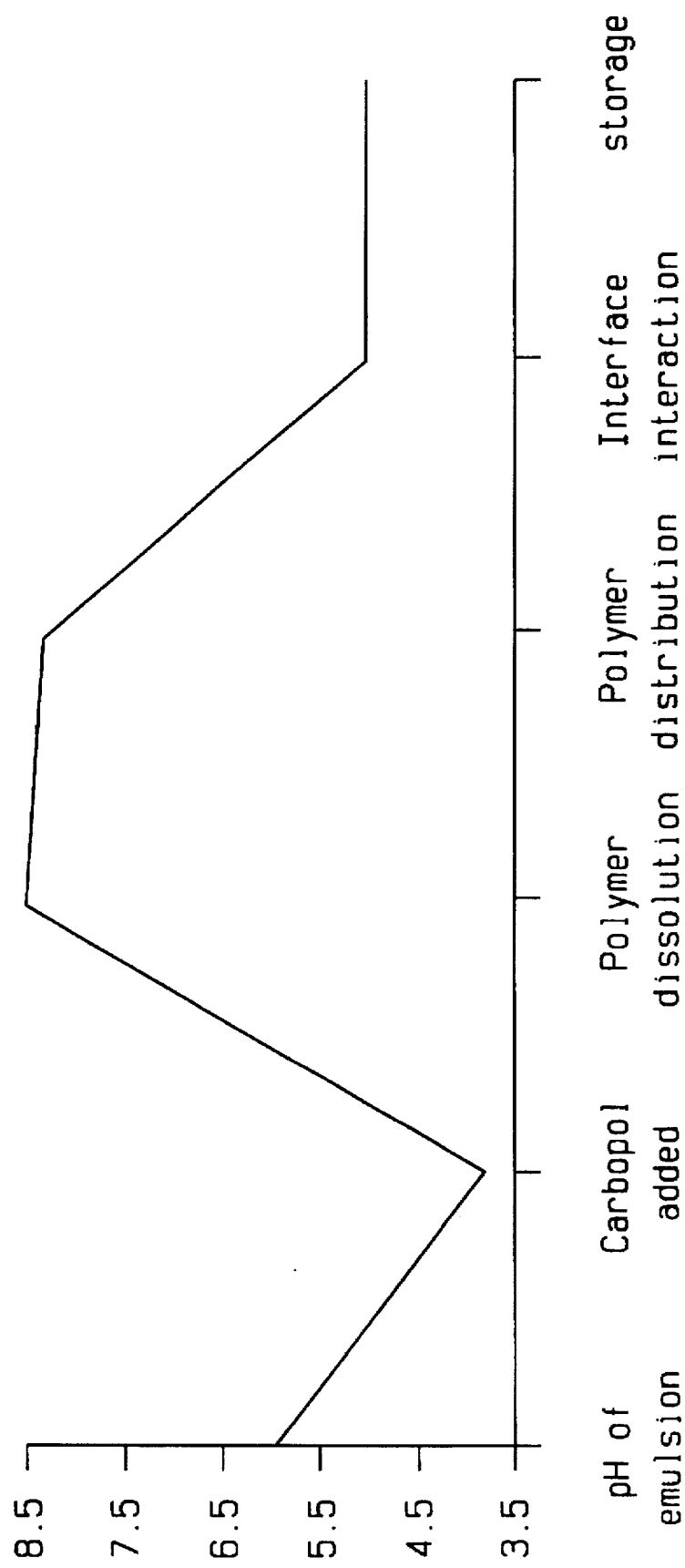
FIG. 2 is a flowchart showing pH changes during the preparation of an exemplary bioadhesive emulsion wherein Carbopol is the bioadhesive polymer.

For polyanionic polymers, the pH is adjusted to an intermediate value not less than pKa+2, preferably pKa+3 or higher (in the range of 5.6–8.5 for polycarboxylic acid polymers), thereby producing substantial to essentially complete dissociation or ionization of the carboxylic acid groups; subsequently the pH of the final preparation is adjusted to 3–7, more commonly 3.5–6.0, to enhance the mucin-binding interaction. The pH profile obtained during one preparation by this procedure of an exemplary emulsion using Carbopol as the mucoadhesive polymer is shown in FIG. 2.

Although the pKa of a polyionic polymer is a sum of multiple pKas, the average pKa values for polymers are comparable to those for the corresponding monomeric structure.

In the case of polycationic polymers such as chitosan, the desired intermediate pH range will be at least pKa-2, preferably pKa-3 or less, corresponding even to pH below 3 for chitosan; the pH may be elevated to a more biologically compatible value, e.g. pH 6–8, after the final emulsion is formed.

When manufacture of emulsions with ionic bioadhesive polymers is attempted under other conditions not utilizing pH changes, bioadhesive polymers sometimes form a water-insoluble interpolymer complex with the surfactants, which leads to the breakdown of the emulsion.

6. Examples: Preparation of Bioadhesive Emulsions

The invention is illustrated by the following non-limiting examples.

6.1. Example 1. Pilocarpine in Oil in Water Emulsion with 2% Miranol and 0.05% Carbopol 420 ml of distilled water in which were dissolved 0.250 g Carbopol-940 (Goodrich, U.S.) and 11.2 g glycerol (isotonic agent), pH 3.82, were warmed to 45° C. and mixed with the oil phase, consisting of 10.5 g pilocarpine (as a base), 21.2 g MCT oil (medium chain triglycerides, SIO, France), 3.75 g Lipoid E-75 (egg lecithin) and 7.8 g Miranol MHT (Lauroamphoacetate, Rhone-Poulenc, France), at a temperature of 60° C. After addition of the pilocarpine base, the pH reached pH 7.8–8.0. After mixing by high speed stirrer (Polytron 3000, Kinematica, Switzerland) at 20,000 rpm for 5 minutes the mixture was dispersed by a high-pressure homogenizer (Gaulin Microlab 70) at 700 bar for 5 minutes (approximately 10 cycles). The resulting emulsion was cooled, and 50 mg of thimerosal and 1.0 g chlorbutanol in 50 ml of water were added as preservatives. After adjusting the pH to 5.0, the emulsion was filtered and packed in sterile bottles.

6.2. Example 2. Pilocarpine in Oil/Water Emulsion with 2% Miranol Without Carbopol The pilocarpine emulsion was prepared as in Example 1, but without Carbopol dissolved in the aqueous phase.

6.3. Example 3. 5% Oil in Water Emulsion with 1.5% Emulfor, with and without Carbopol The aqueous phase was prepared as in Example 1. The oil phase consisted of 21.2 g MCT oil and 3.7 g lecithin. Emulsion preparation was carried as in Example 1. After filtering, droplet size was measured by the photon correlation spectroscopy using a particle size analyzer (N4MD, Coulter Electronics, U.S.A.). The droplet size for carbopol containing droplets was 127±79 nm, and was 52±16 nm for droplets without Carbopol.

6.4. Example 4. 2% Pilocarpine Hydrochloride in Oil/Water Emulsion with 1.5% Tyloxapol and 0.1% Carbopol The aqueous phase consisted of pilocarpine hydrochloride (1.0 g), tyloxapol (0.75 g), Carbopol 940 (added as 5 ml of a 5% water solution), 0.5 g glycerol as isotonic agent, 0.1 g chlorobutanol and 0.005 g thimerosal as preservatives, and 40 ml of distilled water. The solution was adjusted to pH 5.9–6.5 with 0.05M NaOH. The clear solution obtained was mixed with 2.5 g of the warm (450) oil phase, consisting of 87% MCT oil and 13% (by weight) lecithin. The mixture was homogenized by Polytron (20,000 rpm, 5 minutes), and subsequently by high pressure homogenizer (Microlab 70, APV) (800 bar, 6–8 cycles). The pH was adjusted to 5.0 and the emulsion was filtered. Mean oil droplet size (N4MD) was 48±33 nm.

6.5. Example 5. 2% Pilocarpine Hydrochloride in Oil in Water Emulsion with 1.5% Tyloxapol without Carbopol The method of preparation and composition was as in Example 4, but without Carbopol. Mean oil droplet size (N4MD) was 50±41 nm.

6.6. Example 6. 0.2% Indomethacin in 10% Oil in Water Emulsion with 1.5% Emulfor EL-620 and 0.1% Carbopol 940

The oil phase consisted of 4.7 g MCT oil, 0.7 g lecithin, and 0.1 g Indomethacin. After heating to 70° C. to complete dissolution of indomethacin, the oil phase was mixed with the water phase (0.75 g Emulfor EL-620, 1.1 g Glycerol, 38 ml distilled water), homogenized by Polytron (23,000 rpm, 5 minutes) and high pressure homogenizer (800 bar, 8 cycles). Carbopol 940 (5 ml of a 1% water solution) was added to the emulsion, and the pH was adjusted, after mixing with the Carbopol solution, from 4.2 to 7.0 by 2.5N NaOH. This emulsion was mixed for 10 minutes, and the pH was then decreased to 5.0 by 2.5N HCl. The final emulsion was filtered and packed into sterile bottles. Mean oil droplet size (N4MD) was 97±24 nm.

6.7. Example 7. 0.2% Indomethacin in 10% Oil in Water Emulsion with 1.5% Emulfor EL-620, without Carbopol The method of preparation and composition was as in Example 4, but without Carbopol. Mean oil droplet size (N4MD) was 94±21 nm.

6.8. Example 8. 0.4% Indomethacin in 20% Oil/water Emulsion with 1.0% TWEEN-80 and 0.1% Carbopol 940

The method of preparation was as in Example 4. The oil phase consisted of 20% MCT oil, 1.2% Lipoid E, and 0.4% indomethacin. 1.0% TWEEN-80, 0.1% Carbopol 940, pH 5.15. Mean oil droplet size (N4MD) was 299±86 nm.

6.9. Example 9. 0.4% Indomethacin in 20% Oil/Water Emulsion with 1.0% TWEEN-80, without Carbopol The method of preparation and composition was as in Example 8, but without Carbopol. Mean oil droplet size (N4MD) was 137±26 nm.

6.10. Example 10. 0.4% Indomethacin in 20% Oil/Water Emulsion with 1.5% Emulfor EL-620 and 0.1% Polyacrylic Acid The method of preparation was as in Example 1. The oil phase consisted of 20% MCT and 1.2% Lipoid E-80 and indomethacin 0.4%. The aqueous phase consisted of 1.0% TWEEN-80, and 0.1% polyacrylic acid (MW 90,000), 2.0 g of a 25% solution in water, pH 5.15 Mean oil droplet size (N4MD) was 170±35 nm.

6.11. Example 11. 1.0% Diclofenac in 20% Oil/Water Emulsion Cream with 1.0% Emulfor EL-620 and 0.5% Carbopol 940

The oil phase, consisting of 74.4 g MCT oil, 2.65 lecithin, 4.0 g diclofenac (diethylammonium salt) was warmed to 65° C. and mixed with the aqueous phase, consisting of 5.25 g emulfor and 7.85 g glycerol in 256 ml water. The mixture was subjected to Polytron homogenization (24,000 rpm, 5 minutes) and dispersed by high-pressure homogenizer at 700 bar (8 cycles). After cooling, the pH of this emulsion was adjusted to 5.45.

To 2.0 g of a 5% Carbopol 934 solution in distilled water, 18 g of the diclofenac emulsion was added, mixed well by Polytron (7000 rpm, 2 minutes) and the pH was adjusted to 6.0. A soft, gel-like cream was packed into tubes.

6.12. Example 12. 1.0% Diclofenac 1.0% in 20% Oil/Water Cream with Emulsifying Wax A mixture of 0.348 g diclofenac (diethylammonium salt, equal to 0.3 g of the diclofenac base), 5.0 g MCT oil, and 3.0 g emulsifying wax (9 parts of cetostearyl alcohol, 1 part sodium dodecyl sulfate) was warmed to 70° C. To this mixture 25 ml of boiling water was added with vigorous mixing. After cooling, a soft cream was obtained.

7. Example: Efficacy Testing

Tests demonstrating the efficacy of mucoadhesive pharmaceutical emulsions of the present invention are described in the following non-limiting examples.

Figure 3:
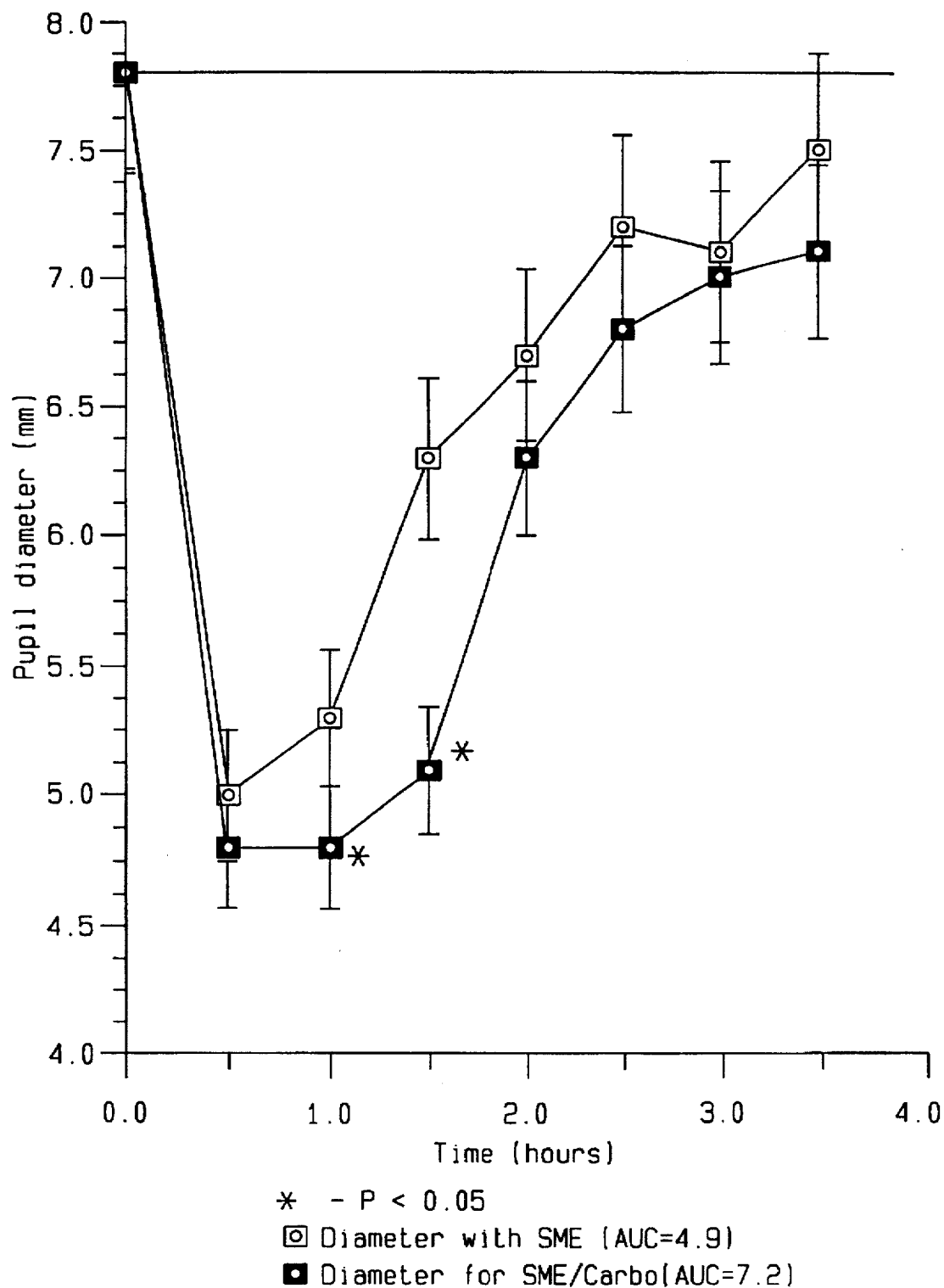
FIG. 3 is a graph showing the change in pupil diameter versus time after intraocular administration of the pilocarpine emulsion of Example 13.
Figure 4:
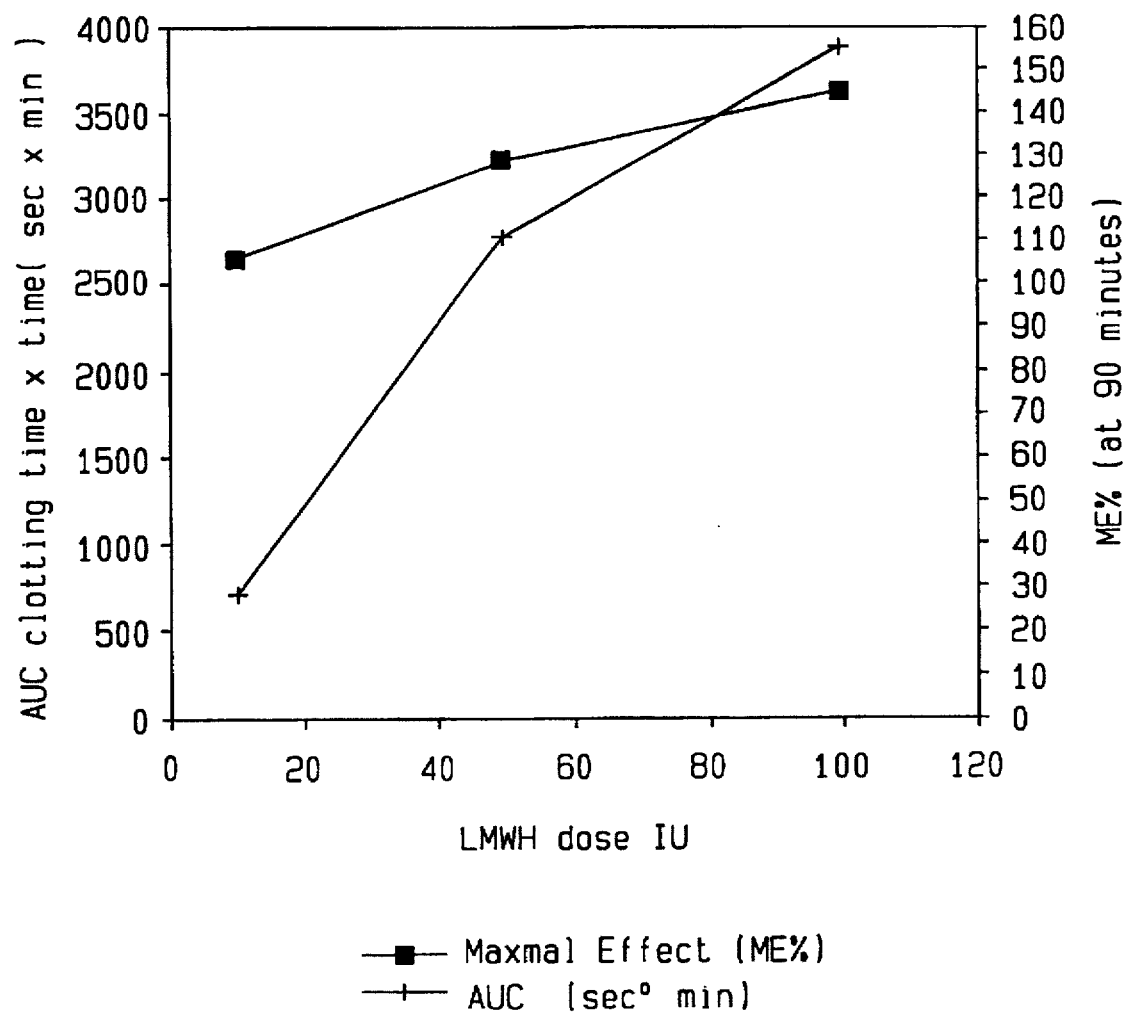
FIG. 4 shows the approximately linear dose-response of blood clotting time and maximal effect, ME %, versus dose of i.v. treatment with low molecular weight heparin (LMWH), for groups A–C of Example 27.
Figure 5:
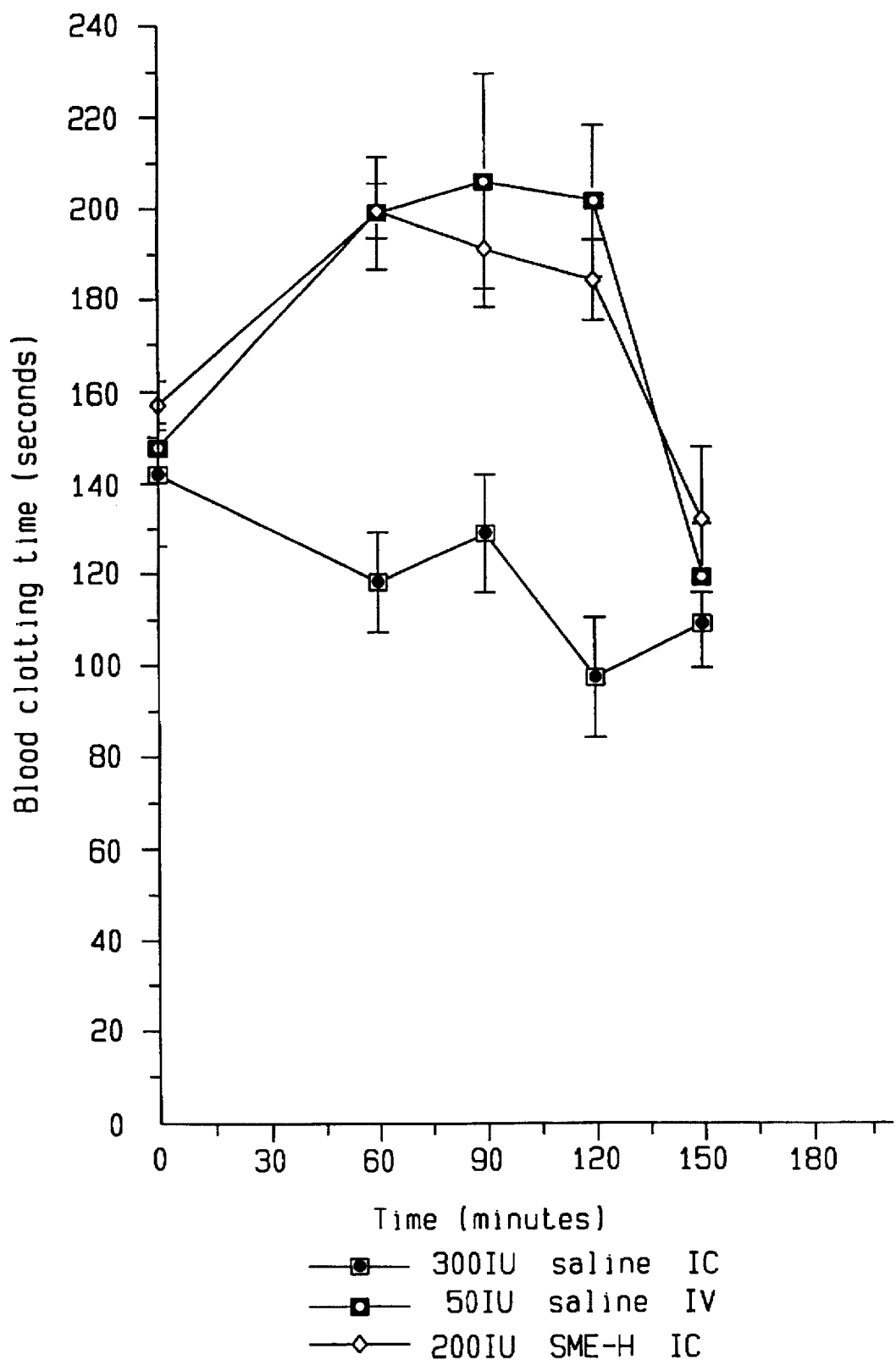
FIG. 5 is a profile of blood clotting time over post treatment time after colonic administration of LMWH in saline versus SME and versus i.v. treated rats, for groups B, E, and G.
Figure 6:
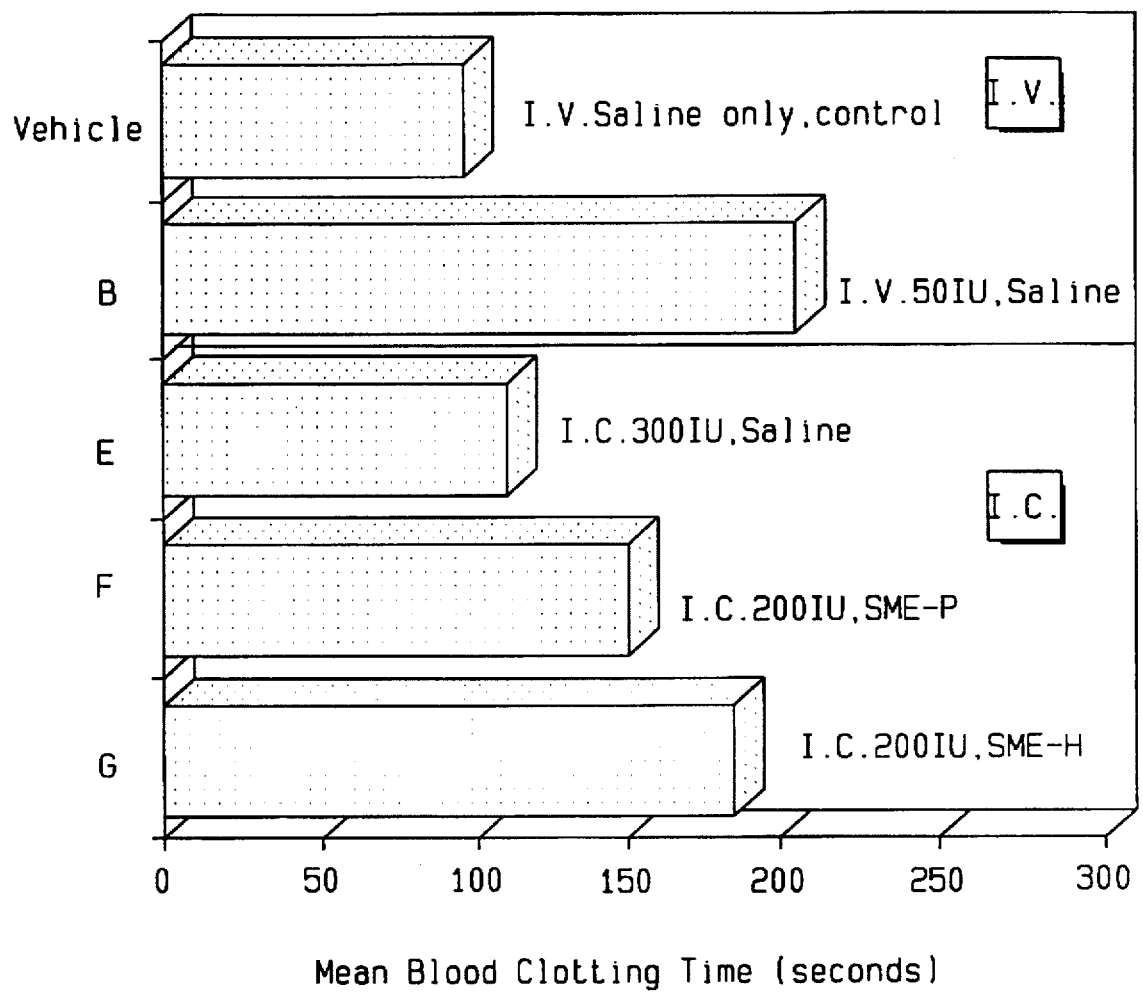
FIG. 6 shows the blood clotting time at $T_{MAX}$ (90 minutes) for the indicated routes of administration and vehicles used to deliver the LMWH.

7.1. Example 13. Prolonged Miotic Activity of Pilocarpine in Bioadhesive Emulsion Miotic response was tested in New Zealand White rabbits after instillation of 50 ml of 1.7% pilocarpine base (2% as pilocarpine HCl) in bioadhesive emulsion (Example 4), or in control preparation (pilocarpine in emulsion, Example 5) in the left eye. Data showing changes in pupil diameter are presented in Table 1 and in graphic form in FIG. 3.

A bioadhesive emulsion of pilocarpine was 45% more effective when compared with pilocarpine in emulsion without bioadhesive properties (7.25/4.98=1.45). The bioadhesive emulsion had more pronounced and prolonged miotic action.

TABLE 1

Pupil Diameter Decrease After Instillation of Pilocarpine in Emulsion (A) and in Bioadhesive Emulsion (B)

| Time (hrs) | Pilocarpine 2% in Emulsion A | Pilo 2% Emulsion + 0.1% carbo. B | Relative Difference, % (B − A)/B |
|---|---|---|---|
| 0 | 0 | 0 | — |
| 0.5 | −2.8 | −3 | 7 |
| 1.0 | −2.5 | −3 | 17 |
| 1.5 | −1.5 | −2.7 | 44 |
| 2.0 | −1.1 | −1.5 | 27 |
| 2.5 | −0.6 | −1 | 40 |
| 3.0 | −0.7 | −0.8 | 13 |
| 3.5 | −0.3 | −0.7 | 57 |
| 4.0 | −0.2 | −0.9 | 78 |
| 4.5 | −0.1 | −0.4 | 75 |
| 5.0 | 0 | −0.5 | 100 |
| 5.5 | 0 | 0 | — |

Mean values in rabbits, n = 6

Viscosity measurements of pilocarpine emulsions with and without bioadhesive polymer (see Table 2) demonstrate that bioadhesive properties of such preparations are essentially due to polymer-surface interaction, rather than to increased viscosity.

Increased retention time while in the eye or increased effective drug concentration can be tested directly by different methods.

TABLE 2

Viscosity of Emulsions With and Without 0.1% Carbopol

| % Pilo-HCl | % Carbopol | Droplet Size, nm | pH | Viscosity cP(*) | Relative (**) |
|---|---|---|---|---|---|
| 2 | 0.1 | 82.5 ± 30 | 5.00 | 1.5 | 1.11 |
| 0 | 0.1 | 75.7 ± 28 | 5.02 | 1.7 | 1.21 |
| 2 | 0.0 | 81.2 ± 33 | 4.99 | 1.4 | 1.04 |
| 0 | 0.0 | 78.4 ± 26 | 5.04 | 1.35 | 1 |

(*)Measured at 25.7°; Spindel ULA ode #00; 60 RPM; Water viscosity = 1 cP
(**)Viscosity of 0.1% Carbopol emulsion/viscosity of blank emulsion

7.2. Example 14: Enhanced Drug Penetration Through Cornea

A 0.4% indomethacin in emulsion with (Example 8) or without (Example 9) a bioadhesive polymer coating was applied onto the corneal surface of the eye by micropipette in a volume of 50 ml. Liquid samples from the anterior chamber were taken by microsyringe. The indomethacin concentration was determined by an HPLC method. The intraocular concentrations obtained are summarized in Table 3. A 1% Indomethacin suspension (Indoptic, MSD) was used as a reference preparation. Indoptic is one of the most widely prescribed product in the ocular nonsteroidal anti-inflammatory drug market.

As shown in Table 3, indomethacin in bioadhesive emulsion is significantly more effective for drug delivery into the eye as compared with the emulsion without bioadhesive polymer. The maximal concentration in the anterior eye chamber is 1.7 times higher (mean value 3.35 nM at 1 hour versus 2.04 mM at 45 minutes), and the area under the curve (AUC) (i.e., the cumulative quantity of drug delivered into the eye) is more than 1.6 times higher (AUC=10.39 versus 6.305) for the bioadhesive composition. By comparison, the 1% commercial indomethacin suspension (Indoptic) provides an AUC value of only 4.49.

TABLE 3

Indomethacin in Emulsions With and Without Carbopol: Drug Penetration into the Eye After Topical Instillation of 50 μl

Indomethacin Concentration in the Anterior Eye Chamber

| Time (Hrs) | 0.4% Emulsion | S.D. | 0.4% Emul/carbo | S.D. | 1% Indoptic MS&D | S.D. |
|---|---|---|---|---|---|---|
| 0 | 0 | 0 | 0 | 0 | 0 | 0 |
| 0.25 | 0.96 | 0.44 | 1.24 | 0.91 | 0.23 | 0.03 |
| 0.5 | 1.35 | 0.87 | 2.44 | 1.11 | 2.2 | 1.7 |
| 0.75 | 2.04 | 0.8 | 2.99 | 0.8 | 1.54 | 0.51 |
| 1 | 1.86 | 0.86 | 3.35 | 0.95 | 0.97 | 0.56 |
| 3 | 0.89 | 0.4 | 1.57 | 0.94 | 0.57 | 0.23 |
| 6 | 0.2 | 0.09 | 0.23 | 0.1 | 0.22 | 0.12 |
| 12 | 0 | 0 | 0 | 0 | 0 | 0 |
| AUL | 6.305 | | 10.4 | | 4.499 | |

7.3. Interaction of Bioadhesive Polymers with Oil Surface Absorbed Surfactants

7.3.1. Example 15. Emulsion Containing mineral Oil, Lecithin, and Carbopol

The acidic polymer consisted of Carbopol (polyacrylic acid, MW 1–4 million). The oil phase was a mineral oil and lecithin emulsion with mineral oil and Lipoid E-75 in a 9:1 ratio. The aqueous phase consisted of 0.05% Carbopol 940 and 1% TWEEN-80 in water with pH 6.5 at a temperature of 25.4° C. Viscosity data for 0.05% Carbopol in water, 19.7 cP; 0.05% Carbopol in 1% TWEEN-80, 13.6 cP; 10% oil phase in 1% TWEEN-80 without Carbopol, 1.6 cP (242±200 nm). The 10% oil phase consisted of 0.05% Carbopol/1% TWEEN-80, 1.9 cP (150±48 nm).

7.3.2. Example 16. Emulsion Containing Long Chain Triglyceride (LCT, Soya Oil) and Emulfor The oil phase consisted of LCT:Emulfor EL-620 9:1. The aqueous phase consisted of 0.1% Carbopol 940 in water with 6.0 pH at 25.5° C. The viscosity data showed for 0.1% Carbopol in water, 89.3 Cp; 0.1% Carbopol in 2% Emulfor, 57.9 cP; 10% oil phase without polymer, 1.4 cP (168+49 nm); 10% oil phase in 0.1% Carbopol, 2.7 cP (183+57 nm).

7.3.3. Example 17. Emulsion Containing Carboxymethylcellulose, Mineral Oil and PEG-stearate as Surfactant The oil phase consisted of mineral oil: Simulsol M53 (PEG 50—stearate, "Seppic", France) 9:1. The aqueous phase consisted of 0.2% carboxymethylcellulose (MW about 100,000) in water with pH 5.2 at 25.7° C. The viscosity data showed for 0.2% CMC in water, 6.3 cP; 10% oil phase without polymer, 1.3 cP (407+140 nm); 10% oil phase in 0.2% CMC, 3.0 cP (439+160 nm).

7.3.4. Example 18. Emulsion Containing Isopropylmyristate and TWEEN-80

The oil phase consisted of isopropyl myristate: TWEEN-80 9:1. The aqueous phase consisted of 0.2% carboxymethylcellulose (MW about 100,000) in water with a pH 5.0 and a 25.1° C. The viscosity data for 0.2% CMC in water, gave 6.2 cP; 10% oil phase without polymer, 1.6 cP (89+43 nm); 10% oil phase in 0.2% CMC, 3.0 cP (94+33 nm).

7.3.5. Example 19. Emulsion Containing Mineral Oil, Lecithin, 1% TWEEN-80, with 0.1% and 0.2% Alginate The oil phase consisted of mineral oil: Lipoid E-75 9:1. The aqueous phase consisted of 0.1% alginic acid (Na salt, medium viscosity) in 1% TWEEN-80 and 0.2% alginic acid (Na salt, medium viscosity) in 1% TWEEN-80 with pH 5.2 at 25.5° C. The viscosity data for 0.1% alginic acid, gave 7.6 cP; 0.2% alginic acid, 10.7 cP; 10% oil phase in 1% TWEEN-80, 1.3 cP (202+62 nm); 10% oil phase in 0.1% alginic acid/TWEEN-80, 4.8 cP (171+55 nm); 10% oil phase in 0.2% alginic acid/TWEEN-80, 10.6 cP.

7.3.6. Example 20. Emulsion with Basic polymer: Chitosan

The oil phase consisted of MCT oil with Lipoid E80 (9:1). The aqueous phase consisted of 0.5% chitosan in 1% TWEEN-80 at pH 2.1 and 24.8° C. Viscosity data for 0.5% chitosan, gave 43.5 cP; 10% oil phase in 0.1 chitosan/TWEEN-80, 18.6 cP (101+43 nm).

7.3.7. Example 21. Emulsion with Neutral (Non-charged) Polymer: Hydroxypropylmethylcellulose (HPMC 4000)

The oil phase consisted of MCT oil with Lipoid E80 (9:1). The aqueous phase consisted of 0.2% HPMC in 1% TWEEN-80 at pH 6.0 and 27.2° C. The viscosity data for 0.2% HPMC in water, gave 4.0 cP; 10% oil phase without polymer, 1.6 cP (89±43 nm); 10% oil phase in 1% TWEEN-80/0.2 HMC, 2.4 cP (110±37 nm).

7.3.8. Evaluation of Interaction of Bioadhesive Polymers with Surfactants

Interaction between bioadhesive polymer and surface absorbed amphiphilic surfactants was evaluated with the several different polymers, surfactants, and oils which are described in the above examples and summarized in Table 4. As reflected by the viscosity data, carboxymethylcellulose (MW about 100,000) and alginic acid (MW about 70,000) demonstrated lower interaction with the surfactant layer than did Carbopol. Use of a non-ionic surfactant alone, without lecithin, does not lead to pronounced decrease of interaction force and formation of outer polymer layer around oil droplet. Many types of oil—paraffin (mineral) oil, esters such as isopropylmyristate, long chain triglycerides, and others—are almost equally suitable for bioadhesive emulsion formation. Interestingly, the results with alginic acid demonstrate that if the concentration of bioadhesive polymer is higher than the concentration necessary for partial interaction with surfactant, there is no difference between samples with and without surfactant. This result indicates formation of a complex between polymer and the polar head of amphiphilic surfactants (e.g., the ethylene oxide chain or phosphatidyl group). Interaction of the surfactant interface with non-charged polymers, such as hydroxypropylmethycellulose, is less pronounced, but nevertheless significant.

7.3.9. Example 22. Non-bioadhesive Polymer Demonstrates Lack of Interaction with Emulsion To a prepared emulsion containing 10% MCT oil, 1.5% lecithin, 1% Emulfor EL-620, 1% dry dextran T-70 (poly-1,6-glucoside, molecular weight about 70,000 Dalton) was added, and the mixture was stirred until complete dissolution of polymer. Viscosity data (see Table 5) indicate the absence of any interaction between dextran and oil droplets in emulsion. Viscosity of an emulsion with dextran is approximately the sum of the viscosities of the emulsion and the dextran solution. By contrast, in all cases of bioadhesive polymers, interaction of the polymer with oil droplet interface leads to significantly reduced viscosity of emulsions with added bioadhesive polymer. For comparison, 0.1% Carbopol in solution gives relatively high viscosity (see Table 4); with added SME, the viscosity decreases due to specific interaction of the polymer with the emulsion.

TABLE 4

Bioadhesive Polymers Interaction with Emulsion

| Polymer | Conc % | Oil | Surfactant | % Surf | % Lecth | pH | Visc cP | Size nm | S.D. | Temp C. |
|---|---|---|---|---|---|---|---|---|---|---|
| Carbopol | 0.05 | | | | | 6.5 | 19.7 | | | 25.4 |
| Carbopol | 0.05 | | TWEEN-80 | 1 | | 6.5 | 13.6 | | | |
| | | Mineral | TWEEN-80 | 1 | 1 | 6.5 | 1.6 | 242 | 200 | |
| Carbopol | 0.05 | Mineral | TWEEN-80 | 1 | 1 | 6.5 | 1.9 | 150 | 48 | |
| Carbopol | 0.1 | | | | | 6.0 | 89.3 | | | 25.5 |
| Carbopol | 0.1 | | Emulfor EL-620 | 2 | | 6.0 | 57.9 | | | |
| | | LCT | Emulfor EL-620 | 2 | | 6.0 | 1.4 | 168 | 49 | |
| Carbopol | 0.1 | LCT | Emulfor EL-620 | 2 | | 6.0 | 2.7 | 183 | 57 | |
| CMC** | 0.2 | | | | | 5.2 | 6.3 | | | 25.7 |
| | | Mineral | Simulsol M-53 | 1 | | 5.2 | 1.3 | 407 | 140 | |
| CMC | 0.2 | Mineral | Simulsol M-53 | 1 | | 5.2 | 3.0 | 439 | 160 | |
| CMC | 0.2 | | | | | 5.0 | 6.3 | | | 25.1 |
| CMC | 0.2 | | TWEEN-80 | 1 | | 5.0 | 5.4 | | | |
| | | IPM* | TWEEN-80 | 1 | | 5.0 | 1.6 | 89 | 43 | |
| CMC med. | 0.2 | IPM | TWEEN-80 | 1 | | 5.0 | 3.0 | 94 | 33 | |
| Alginic Acid | 0.1 | | | | | 5.2 | 7.6 | | | 25.5 |
| Alginic Acid | 0.1 | | TWEEN-80 | 1 | | 5.2 | 6.9 | | | |
| Alginic Acid | 0.2 | | | | | 5.2 | 10.7 | | | |
| | | Mineral | TWEEN-80 | 1 | 1 | 5.2 | 1.3 | 202 | 65 | |
| Alginic Acid | 0.1 | Mineral | TWEEN-80 | 1 | 1 | 5.2 | 4.8 | 171 | 55 | |
| Alginic Acid | 0.2 | Mineral | TWEEN-80 | 1 | 1 | 5.2 | 10.6 | | | |
| Chitosan med. | 0.5 | | | | | 2.1 | 43.5 | | | 27.1 |
| Chitosan med. | 0.5 | MCT | TWEEN-80 | 1 | 1 | 2.1 | 18.6 | 101 | 43 | |
| HPMC 4000 | 0.2 | | | | | 6.0 | 4.0 | | | 26.1 |
| HPMC 4000 | 0.2 | | | | | 6.0 | 3.6 | | | |
| | | MCT | TWEEN-80 | 1 | 1 | 6.0 | 1.6 | 89 | 43 | |
| HPMC 4000 | 0.2 | MCT | TWEEN-80 | 1 | 1 | 6.0 | 2.4 | 110 | 37 | |

*IPM = Isopropylmyristate; TWEEN-80 - Polyoxyethylene Sorbitane Monooleate; Emulfor - Polyoxyethylated Ricinic Oil; Simulsol M-53 - Polyoxyethylated Stearic Acid (PEG50 Stearate)
**CMC = Medium Molecular Weight, Carboxy Methyl Cellulose

TABLE 5

Non-bioadhesive Polymer Demonstrates Lack of Interaction with Emulsion

| Preparation | Viscosity at 37° C., cP |
|---|---|
| 1% Dextran T-70 in water | 1.3 |
| 1% Dextran T-70 in 1% Emulfor EL-620 | 1.3 |
| Plain Emulsion, 10% Oil Phase | 1.3 |
| Plain Emulsion + 1% Dextran T-70 | 1.3 |

7.3.10. Example 23. Preparation of Unstable Emulsion with Pilocarpine and Carbopol Examples 23 and 24 demonstrate that certain other methods of preparation do not yield useful bioadhesive emulsions, but rather lead to instability and breakdown of the emulsion.

An attempt to make a polyacrylate emulsion without adjusting the pH to a value well above the pKa produced a broken emulsion of pilocarpine hydrochloride 2% in oil/water emulsion with 1.5% Tyloxapol and 0.1% Carbopol (similar to the emulsion of Example 4). The aqueous phase combined the components of pilocarpine hydrochloride (1.0 g), Carbopol 940 (added as 5 ml of a 5% water solution), glycerol (0.5 g) as isotonic agent, chlorobutanol (0.1 g) and thimerosal (0.005 g) as preservatives, and 40 ml of distilled water. These components were mixed together and stirred until complete dissolution. The pH value of the water phase was 3.8. The clear solution obtained was mixed with the warm (45° C.) oil phase, consisting of MCT oil (2.175 g), lecithin (0.325 g) and Tyloxapol (0.75 g). The mixture was homogenized by Polytron (200,000 rpm, 5 minutes) and by high pressure homogenization (Microlab 70, APV at 800 bar, 6–8 cycles). The pH after homogenization was adjusted to 5.0 with 1N NaOH. The resulting emulsion was impossible to filter through 0.2, 0.45, or 1.2 micron filters.

Mean droplet size (N4MD) was 568 nm, with a broad size distribution. Analysis of SDP weight showed two populations of 96±34 nm (13%) and 930±1360 nm (87%), with 9% dust. After two days of storage at room temperature or 4° C., the emulsion was completely broken down, and exhibited phase separation and the presence of polymer flake residue.

7.3.11. Example 24. Preparation of Unstable Emulsion with Indomethacin and Carbopol An attempt to make a polyacrylate emulsion by raising the pH to a value only slightly greater than the pKa also produced a broken emulsion containing indomethacin 0.2% in 10% oil/water emulsion with 1.5% Emulfor EL-620 and 0.1% Carbopol 940 (similar to the emulsion of Example 6).

The oil phase, consisting of 4.7 g MCT oil, 0.7 g lecithin, and 0.1 g indomethacin, was heated to 70° C. to complete the dissolution of indomethacin, mixed with the water phase (0.75 g Emulfor EL-620, 1.1 g glycerol and 38 ml distilled water), and homogenized with a Polytron homogenizer (23,000 rpm, 5 minutes) followed by high-pressure homogenization (800 bar, 8 cycles). Carbopol (5 ml of a 1% water solution) was added to the emulsion. After mixing with the Carbopol solution, the pH was adjusted from 4.2 to 5.0 with 2.5N NaOH, and the emulsion was mixed for 10 minutes. The resulting emulsion was unsuitable for filtration and broke down after 24 hours at room temperature. The mean oil droplet size (N4MD) was 1640±980 nm.

7.4. Examples 25 and 26. "Ex Vivo" Model of Intestinal Adsorption from Emulsion Drug Delivery Systems Examples 25 and 26 illustrate intestinal adsorption of Carbopol and chitosan bioadhesive emulsions, respectively. An animal model of intestinal adsorption of colloidal delivery systems was modified from Lehr et al., *J. Controlled Release* 13:51–62 (1990).

Wistar male rats, body weight 250–300 g, after fasting for 16 hours (with water consumption ad libidum) were anesthetized by intraperitoneal injection of ketamine 70 mg/kg and rompun 5 mg/kg. The abdominal wall was cut at the median line, and the peritoneum was opened over the right lateral region of the abdomen. Part of the small intestine (15 cm in length) below the duodenum was ligated by surgical silk. The intestine was catherized with silicone tubes in two places, near the ligature and in the distal end. Catheters were tightly ligated, and the loop was continuously perfused by Dulbecco buffered medium (pH 7.4, temperature 37° C.) using a peristaltic pump until perfusion solution was observed. Control readings were recorded using a flow-through cell and UV-visible spectrophotometer at 600–800 nm (light dispersion region). A measured volume of the test preparation was added to a sample vial, containing Dulbecco buffer, and optical density was tested at the working wavelength. The sample vial was sealed with a stopper, equipped with two silicone tubes for input-output, and inserted into the perfusion loop. Optical density changes were monitored in the flow cell. Experiments were performed with control SME and bioadhesive SME. The emulsions used in these experiments were chosen to have closely similar particle size distribution, and were adjusted to approximately equal initial optical densities at the working wavelength.

A bioadhesive emulsion containing 0.1% Carbopol demonstrated a reproducible decrease in optical density during the first cycle through the ligated intestine loop. The decrease in optical density was significantly more pronounced than that obtained with a plain emulsion of the same composition, but without Carbopol (see Table 6). Analogous data were obtained for emulsions with and without chitosan, a positively charged amino polysaccharide (Table 7).

TABLE 6

Increased Retention of Bioadhesive Carbopol Containing Emulsion versus Plain SME

| Emulsion | AUC | Maximal o.d. |
|---|---|---|
| SME 20% Oil Phase | 2.891 | 0.120 |
| SME 20% Oil Phase Carbopol 0.1% | 2.225* | 0.058* |

(*)The decrease in values denotes increased retention in the ligated segment of the intestine

7.5. Example 27. Increased Colonic Bioavailability of Low Molecular Weight Heparin in Bioadhesive Emulsions Low molecular weight heparin (LMWH; Fragmin, KabiVitrum, Sweden) is a mixture of heparin fragments having an average molecular weight of 4,000–6,000 Da. It is indicated for the treatment or prophylaxis of thromboembolism in peri- and post-operative surgical patients. Currently, heparin and the six presently commercialized heparin fragments are administered only parenterally, by i.v. or subcutaneous injection.

TABLE 7

Increased Retention of Bioadhesive Chitosan Emulsion versus Plain SME

| | AUC | Maximal O.D. |
|---|---|---|
| SME 5% Oil Phase | 0.0516 | 0.188 |
| SME 5% Oil Phase Chitosan | 0.0390* | 0.146* |

(*)The decreased values are indicative of increased retention of the preparation in the intestine

7.5.1. Methods of Preparation of Fragmin SME

Fragmin was incorporated into submicron emulsions (SME) with or without inclusion of a bioadhesive polymer. Fragmin was purchased from KabiVitrum AB as a solution of 5000 IU/0.3 ml. The LMWH SME was mixed with carboxymethylcellulose (CMC, medium weight) to obtain a stable bioadhesive emulsion. These emulsions were stored in lyophilized form and reconstituted prior to use. The reconstituted product had a mean droplet size of 40 nm ±SD.

The following general methods were used for preparation of submicron emulsions containing Fragmin:

a) Extrinsic

SME of Fragmin usually was prepared by adding a Fragmin solution to blank SME and subsequently vortexing the resulting material.

b) Intrinsic

Fragmin was added to the water phase of an oil-water mixture and then treated (4 cycles) in a Gaulin Microlab 70 high pressure homogenizer at 800 bar (cooling on ice between treatments). The concentrations of Fragmin were prepared so that 40–100 μl were injected i.v. and 100–300 μl were injected i.c.

7.5.2. Animal Experiments

Clotting time of blood droplets obtained by tail knick was used to evaluate the systemic effect of LMWH following intracolonic (i.c.) or intravenous (i.v.) treatment of rats. Male Sprague Dawley rats (200–300 g) were used for all of these experiments. Following preliminary studies, experiments were performed between 8:00–13:00 hours in order to reduce diurnal changes in responsiveness to heparins. Rats were anesthetized with 0.3 ml ketalar/rompun (2:1), weighed, and the initial blood clotting time was determined. Each rat was then treated with either Fragmin or control vehicle (i.v. or i.c.). Intravenous treatment was performed by exposing the femoral artery and injecting in the direction of blood flow. Intracolonic treatment was performed by opening the peritoneal cavity at the midline, locating the secum, and injecting into the large intestine, approximately 2 cm from the secum. The time of treatment was considered as $T_o$. At the indicated intervals, blood clotting time was determined.

The pharmacological activity, denoted PA%, was used to evaluate the relative effect of various routes of administration and dose levels on blood clotting time. PA % was calculated for the individual rats and the values presented are the mean of each group. PA% was calculated as follows:

$$PA\ \% = \frac{(AUC_{ic}/D_{ic})}{(AUC_{iv}/D_{iv})} \times 100$$

where AUC is the Area Under the Curve, showing the integrated response over time; D is the dose; ic indicates intracolonic administration, and iv intravenous administration.

7.5.3. Analysis of Blood Clotting

Blood clotting was measured by knicking the tail (beginning from the distal end and progressing forward with each subsequent trial) and collecting the isolated drops on a precleaned glass slide. Pressure was applied to the tail in order to reduce further bleeding. Each droplet was prodded with a 28G needle in an attempt to raise a strand of clotted material. This was done at 10 second intervals on a succession of 3–5 drops until a strand could be raised. The clotting time was measured with a stop watch that was started when the drops were collected.

7.5.4. Results with Fragmin SME

Fragmin (low molecular weight heparin, KabiVitum, Sweden) was incorporated into a 5% oil/water emulsion with 1.5% Emulfor EL-620 and 0.5% carboxymethylcellulose.

Aqueous phase was prepared by dissolution of 0.5% Na-Carboxymethyl-cellulose (MW about 100,000 Da), EDTA disodium dihydrate (0.1%), and Emulfor EL-620 (1.5%) in distilled water. The pH value of the aqueous phase was 7.8. The prepared aqueous phase was mixed together with 5% by weight of oil phase, consisting of MCT oil and egg yolk lecithin (85:15), and homogenized by Polytron (20,000 rpm, 5 minutes) and by high pressure homogenizer (Microlab 70, APV)(800 bar, 6–8 cycles), maintaining the temperature at no more than 55° C. The prepared emulsion was filtered, Fragmin (250 I.U./ml) was added, and the pH was adjusted to 5.0 with 2.5N HCl solution.

The mean oil droplet size (N4MD) was 93±34 nm (unimodal), 0% dust.

For lyophilization of the prepared emulsion, PVP K-15 (1% w/v) and the glycine (4% w/v) were added, and the preparation was freeze-dried under standard conditions.

The results, summarized in Table 8, showed significantly ($p<0.05$) higher absorption of LMWH from the colon when a bioadhesive SME (SME-H) was used as the vehicle.

TABLE 8

Increased Colonic Absorption of LMWH in Bioadhesive SME

| Group | Route | Dose IU/kg | Vehicle | No. of Animals | AUC Sec*Min | Pharmacological Availability PA % | ME % |
|---|---|---|---|---|---|---|---|
| A | i.v. | 10 | Saline | 4 | 708 | 128 | 32 |
| B | i.v. | 50 | Saline | 6 | 2767 | 100[a] | 125 |
| C | i.v. | 100 | Saline | 4 | 3872 | 70 | 199 |
| D | i.v. | 50 | SME | 4 | 2214 | 82 | 142 |
| E | i.c. | 300 | Saline | 4 | 10 | 0 | 1 |
| F | i.c. | 200 | SME | 6 | 1771 | 16 | 66 |
| G | i.c. | 200 | SME-H | 11 | 2753 | 25 | 105 |

[a]Standard I.P. dose for PA % calculation. values are used instead of i.v.

8.0. Incorporation by Reference

To the extent necessary to understand or complete the disclosure of the present invention, all publications, patents, and patent applications mentioned herein are expressly incorporated by reference therein to the same extent as though each were individually so incorporated.

What is claimed:

1. An oil-in-water emulsion for administration of a drug to a mucosal surface, said emulsion comprising a plurality of submicron particles having an average particle diameter of from 10 nm to 600 nm, said particles having a hydrophobic core of a fat or oil which is surrounded by a surfactant layer, and an aqueous continuous phase; said emulsion further including a drug and a mucoadhesive polymer which is a polymer or copolymer of acrylic acid or methacrylic acid, a poly(methyl vinyl ether/maleic anhydride) copolymer, pectin, alainic acid, hyaluronic acid, chitosan, gum tragacanth, karaya gum or carboxymethylcellulose, said hydrophobic core comprising less than 1% (w/w) protein, relative to the weight of the hydrophobic core, and said emulsion comprising less than 5% (w/w) surfactant, relative to the weight of the hydrophobic core.

2. The emulsion of claim 1 wherein said mucoadhesive polymer is a polymer or copolymer of acrylic acid or methacrylic acid.

3. The emulsion of claim 2 wherein said polymer is polyacrylic acid.

4. The emulsion of claim 1 wherein said mucoadhesive polymer is carboxymethylcellulose.

5. The emulsion of claim 1 wherein said mucoadhesive polymer is hydroxypropylmethylcellulose.

6. The emulsion of claim 1 wherein said mucoadhesive polymer is chitosan.

7. The emulsion of claim 1 wherein said mucoadhesive polymer is selected from the group consisting of pectin, alginic acid, hyaluronic acid, gum tragacanth, and karaya gum.

8. The emulsion of claim 1 wherein said hydrophobic core comprises a triglyceride.

9. The emulsion of claim 1 wherein said hydrophobic core comprises paraffin or mineral oil.

10. The emulsion of claim 1 wherein said hydrophobic core comprises silicone oil.

11. The emulsion of claim 1 wherein said hydrophobic core comprises an ester of a fatty acid.

12. The emulsion of claim 1 wherein said core contains less than 1% (w/w) cholesterol.

13. The emulsion of claim 1 wherein said emulsion further comprises a cryoprotectant.

14. The emulsion of claim 13 wherein said cryoprotectant is an amino acid or oligopeptide.

15. The emulsion of claim 1 wherein said cryoprotectant is polyvinylpyrrolidone.

16. The emulsion of claim 1 wherein said surfactant is selected from the group consisting of phosphatidylcholine, phosphatidylethanolamine, phosphatidylserine, phosphatidylinositol, phosphatidylglycerol, cholates, phosphatidic acid, and cardiolipin.

17. The emulsion of claim 16 wherein said surfactant comprises phosphatidylcholine.

18. The emulsion of claim 1 wherein said surfactant is selected from the group consisting of fatty alcohols, polyethylene glycol esters of fatty acids, polyethoxylated fatty acids, polyethoxylated fatty alcohol ethers, polyethoxylated alkylphenyl ethers, SDS, polysorbates, and poloxamers.

19. The emulsion of claim 18 wherein said surfactant comprises a polyethylene glycol ester of a fatty acid.

20. The emulsion of claim 1 wherein said drug is selected from the group consisting of antivirals, steroidal and non-steroidal anti-inflammatory drugs, antibiotics, antifungals, vitamins, hormones, retinoic acid, prostaglandins, prostacyclins, antineoplastic and antimetabolitic drugs, miotics, cholinergics, adrenergic antagonists, anticonvulsants, antianxiety agents, major tranquilizers, antidepressants, anesthetics, analgesics, anabolic steroids, estrogens, progesterones, glycosaminoglycans, polynucleotides and immunomodulators.

21. The emulsion of claim 20 wherein said drug is a glycosaminoglycan.

22. The emulsion of claim 21 wherein said glycosaminoglycan is a low molecular weight heparin.

23. The emulsion of claim 20 wherein said drug is a miotic agent.

24. The emulsion of claim 23 wherein said miotic agent is pilocarpine.

25. The emulsion of claim 20 wherein said drug is an antiinflammatory.

26. The emulsion of claim 25 wherein said antiinflammatory is diclofenac.

27. The emulsion of claim 25 wherein said antiinflammatory is indomethacin.

28. The emulsion of claim 20 wherein said drug is verapamil.

29. The emulsion of claim 1 wherein said emulsion has a pH between 3 and 8.

30. The emulsion of claim 29 wherein said emulsion has a pH between 4 and 6.

31. The emulsion of claim 1 wherein said plurality of submicron particles have an average particle diameter of 30–500 nm.

32. The emulsion of claim 31 wherein said average particle diameter is 70–300 nm.

33. The emulsion of claim 1 wherein said emulsion contains less than 1% (w/w) of an unhalogenated aliphatic C3–C6 alcohol cosurfactant, relative to the weight of the hydrophobic core.

34. The emulsion of claim 1 wherein said emulsion contains less than 1% (w/w) of a monoglyceride cosurfactant, relative to the weight of the hydrophobic core.

35. The emulsion of claim 1 wherein said emulsion contains less than 1% (w/w) of a lysophosphatidylcholine cosurfactant, relative to the weight of the hydrophobic core.

36. The emulsion of claim 1 wherein said emulsion contains less than 1% (w/w) sorbitol, relative to the weight of the hydrophobic core.

37. The emulsion of claim 1 wherein said emulsion contains less than 1% (w/w) milk or serum apolipoprotein, relative to the weight of the hydrophobic core.

38. A dehydrated emulsion for administration of a drug, comprising a drug and the emulsion according to claim 1, in a dehydrated state, whereby a bioadhesive emulsion is generated when water is added to said dehydrated emulsion.

39. A method for administering a drug comprising applying to a mucosal surface an oil-in-water emulsion comprising a plurality of particles having an average particle diameter of from 10 nm to 600 nm, said particles having a hydrophobic core of a fat or oil which is surrounded by a surfactant layer, and an aqueous continuous phase; said emulsion further including a drug and a mucoadhesive polymer which is a polymer or copolymer of acrylic acid or methacrylic acid, a poly(methyl vinyl ether/maleic anhydride) copolymer, pectin, alginic acid, hyaluronic acid, chitosan, gum tragacanth, karaya gum or carboxyethylcellulose, said hydrophobic core comprising less than 1% (w/w) protein, relative to the weight of the hydrophobic core, and said emulsion comprising less than 5% (w/w) surfactant, relative to the weight of the hydrophobic core.

40. An oil-in-water emulsion for administration of a drug to a mucosal surface, said emulsion comprising a plurality of submicron particles having an average particle diameter of from 10 nm to 600 nm, having a hydrophobic core of a fat or oil, surrounded by a surfactant layer, wherein said surfactant comprises 0.01% to 5% by weight of the emulsion, wherein said hydrophobic core comprises less than 1% (w/w) protein, relative to the weight of the hydrophobic core, and said emulsion further includes a drug, and a mucoadhesive polymer which is a polymer or copolymer of acrylic acid or methacrylic acid, a poly(methyl vinyl ether/maleic anhydride) copolymer, pectin, alginic acid, hyaluronic acid, chitosan, gum tragacanth, karaya gum or carboxymethylcellulose, and said emulsion has a pH between about 3 and 8.

41. A method for administering a drug comprising applying to a mucosal surface an oil-in-water emulsion comprising a plurality of particles having an average particle diameter of from 10 nm to 600 nm, having a hydrophobic core of a fat or oil, surrounded by a surfactant layer, wherein said surfactant comprises 0.01% to 5% by weight of the emulsion wherein said hydrophobic core comprises less than 1% (w/w) protein, relative to the weight of the hydrophobic core, and said emulsion further includes, a drug, and a mucoadhesive polymer which is a polymer or copolymer of acrylic acid or methacrylic acid, poly(methyl vinyl ether/maleic anhydride) copolymer pectin, alginic acid, hyaluronic acid, chitosan, gum tragacanth, karaya gum or carboxymethylcellulose, and said emulsion has a pH between about 3 and 8.

42. The emulsion of claim 40 wherein the hydrophobic core of said emulsion comprises oil or fat components with molecular weights below 5,000 Da.

* * * * *